(12) United States Patent
Sinha

(10) Patent No.: US 7,247,720 B2
(45) Date of Patent: Jul. 24, 2007

(54) PHOSPHITYLATION PROCESS

(75) Inventor: Nanda Dulal Sinha, Milford, MA (US)

(73) Assignee: Avecia Biotechnology Inc., Milford, MA (US)

( * ) Notice: Subject to any disclaimer, the term of this patent is extended or adjusted under 35 U.S.C. 154(b) by 100 days.

(21) Appl. No.: 10/531,323

(22) PCT Filed: Oct. 8, 2003

(86) PCT No.: PCT/GB03/04312

§ 371 (c)(1), (2), (4) Date: Oct. 11, 2005

(87) PCT Pub. No.: WO2004/035599

PCT Pub. Date: Apr. 29, 2004

(65) Prior Publication Data

US 2006/0069247 A1    Mar. 30, 2006

Related U.S. Application Data

(60) Provisional application No. 60/418,185, filed on Oct. 15, 2002.

(51) Int. Cl.
*C07H 21/00* (2006.01)
*C07H 19/04* (2006.01)

(52) U.S. Cl. .................. 536/25.33; 536/26.1; 548/206

(58) Field of Classification Search ............. 536/25.33, 536/26.1; 548/206
See application file for complete search history.

(56) References Cited

U.S. PATENT DOCUMENTS 5,034,534 A    7/1991  Milstein 6,275,725 B1    8/2001  Cosman

FOREIGN PATENT DOCUMENTS

WO    WO 03/4512 A1    1/2003

OTHER PUBLICATIONS

Sanghvi et al., "Improved process fro the preparation of nucleosidic phosphoramidites using a safer and cheaper activator", Organic Process Reaserch & Development, 2000, pp. 175-181, No. 3, American Chemical Society.*

* cited by examiner

*Primary Examiner*—Kamal A. Saeed
(74) *Attorney, Agent, or Firm*—Morgan Lewis & Bockius LLP

(57) ABSTRACT

A process for the phosphitylation of an alcohol or thiol with a phosphitylation agent in the presence of an activator is provided. The activator has the formula:

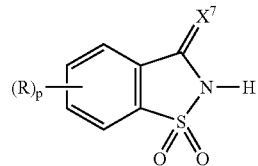

wherein p is 0 or an integer from 1 to 4 and R for each occurrence is a substituent. Preferably $X^7$ is O and p is 0. The activator is commonly employed as a salt complex with an organic base. Preferred alcohols or thiols include nucleosides and oligonucleotides. The process is particularly suited for the synthesis of phosphoramidites.

13 Claims, No Drawings

PHOSPHITYLATION PROCESS

This is a 371 filing based on PCT/GB2003/004312, filed Aug. 10, 2003 and claims the benefit of U.S. Provisional Application No. 60/418,185, filed Oct. 15, 2002.

The present invention concerns a process for the phosphitylation of an alcohol or thiol, and particularly the phosphitylation of a nucleoside to form a nucleoside phosphoramidite.

Synthetic oligonucleotides are important diagnostic tools for the detection of genetic and viral diseases. In addition, oligonucleotides and modified oligonucleotides are of interest as therapeutic candidates that inhibit gene expression or protein function. Large scale synthesis of oligonucleotides for use as therapeutic candidates has become increasingly important since FDA approval of an oligonucleotide analog for the treatment of cytomegalovirus (CMV), and several other oligonucleotide analogs are currently in clinical trials. Kilogram quantities of a purified oligonucleotide analog are needed for each clinical trial.

The principal method currently employed for the preparation of oligonucleotide is the phosphoramidite approach. The increasing demand for larger quantities of oligonucleotides has correspondingly increased demand for phosphoramidite compounds. Phosphoramidite compounds are commonly prepared by phosphitylation of a nucleoside with a phosphitylation agent in the presence of an activator. The most commonly used activator is the nucleophilic activator 1H-tetrazole. However, 1H-tetrazole is explosive and therefore can be hazardous to use in large scale syntheses.

Non-explosive activators that promote phosphitylation and which may be employed without increasing side products are needed in order to make oligonucleotides more readily available for diagnostic and therapeutic use.

According to the present invention, there is provided a process for the phosphitylation of an alcohol or thiol with a phosphitylation agent in the presence of an activator, characterised in that the activator has the formula 1:

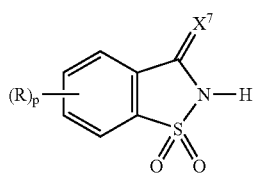

In formula 1, p is 0 or an integer from 1 to 4. R for each occurrence is a substituent, preferably each independently, a halo, a substituted or unsubstituted aliphatic group, $-NR^1R^2$, $-OR^3$, $-OC(O)R^3$, $-C(O)OR^3$, cyano, a substituted or unsubstituted aryl, a substituted or unsubstituted heterocyclyl, $-CHO$, $-COR^3$, $-NHCOR^3$, a substituted or unsubstituted aralkyl, halogenated alkyl (e.g., trifluoromethyl and trichloromethyl), or $-SR^3$.

Preferably, R is halo, a substituted or unsubstituted aliphatic group, $-NR^1R^2$, $-OR^3$, $-OC(O)R^3$, $-C(O)OR^3$, or cyano. Alternatively, two adjacent R groups taken together with the carbon atoms to which they are attached form a six membered saturated or unsaturated ring, preferably an aromatic ring. $R^1$ and $R^2$ are each, independently, $-H$, a substituted or unsubstituted aliphatic group, a substituted or unsubstituted aryl group, a substituted or unsubstituted aralkyl group; or together with the nitrogen to which they are attached form a heterocyclyl group. $R^3$ is a substituted or unsubstituted aliphatic group, a substituted or unsubstituted aryl group, or a substituted or unsubstituted aralkyl group. X is O or S. Preferably, X is O. It is particularly preferred that X is O and p is 0.

Preferably the compound of formula 1 is employed as a salt complex with an organic base.

In many embodiments, the alcohol or thiol is a nucleoside or oligonucleotide comprising a free hydroxy or thiol group, and includes nucleosides and oligonucleotides comprising natural nucleoside pentose sugars and unnatural nucleoside sugars, such as hexoses. When the alcohol or thiol is a nucleoside or oligonucleotide, it is often a protected deoxyribonucleoside, protected ribonucleoside, protected oligodeoxyribonucleotide, protected oligoribonucleotide or a protected oligonucleotide having a mixture of deoxyribonucleotide and ribonucleotide moieties each comprising a free 3'- or 5'-, preferably a 3'-, hydroxy or thiol group, and most preferably a 3'-hydroxy group.

Alcohols and thiols which can be phosphitylated by the process of the present invention include compounds having the formula 2:

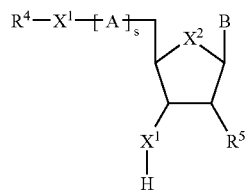

where A represents

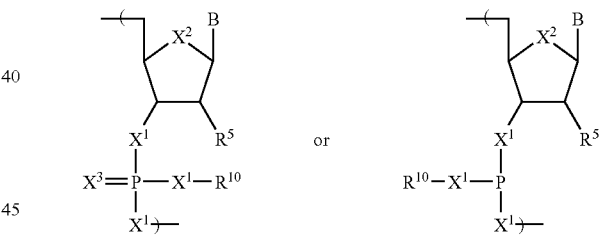

wherein $X^1$ for each occurrence is, independently, $-O-$ or $-S-$. Preferably, $X^1$ is $-O-$ at every occurrence. $X^2$ for each occurrence is, independently, $-O-$, $-S-$, $-CH_2-$, or $-(CH_2)_2-$.

Preferably, $X^2$ is $-O-$ at every occurrence. $X^3$ for each occurrence is, independently, O or S. In a more preferred embodiment, $X^1$ and $X^2$ are each $-O-$ at every occurrence. $R^4$ is an alcohol protecting group or a thiol protecting group. Preferably, $R^4$ is an acid labile protecting group. $R^5$ for each occurrence is, independently, $-H$, $-F$ $-OR^6$, $-NR^7R^8$, $-SR^9$, or a substituted or unsubstituted aliphatic group, such as methyl or allyl. $R^{10}$ for each occurrence is, independently, a phosphorus protecting group, commonly a cleavable phosphorus protecting group employed in oligonucleotide synthesis, and preferably a substituted or unsubstituted aliphatic group, a substituted or unsubstituted aryl group or a substituted or unsubstituted aralkyl group, such as a group of formula $-CH_2CH_2CN$, $-CH_2CH_2CN$, —CH$_2$CH$_2$—Si(CH$_3$)$_2$C$_6$H$_5$, —CH$_2$CH$_2$—S(O)$_2$—CH$_2$CH$_3$, —CH$_2$CH$_2$—C$_6$H$_4$—NO$_2$, —CH$_2$CH$_2$—Si(CH$_3$)$_2$ C$_6$H$_5$, —CH$_2$CH$_2$—S(O)$_2$—CH$_2$CH$_3$, or —CH$_2$CH$_2$—C$_6$H$_4$—NO$_2$. R$^6$ for each occurrence is, independently, —H, a substituted or unsubstituted aliphatic group (e.g., methyl, ethyl, methoxyethyl or allyl), a substituted or unsubstituted aryl group, a substituted or unsubstituted aralkyl, an alcohol protecting group, especially a base-labile or a silyl protecting group, or —(CH$_2$)$_q$—NR$^{11}$R$^{12}$. R$^7$ and R$^8$ for each occurrence are each, independently, —H, a substituted or unsubstituted aliphatic group, or an amine protecting group. Alternatively, R$^7$ and R$^8$ taken together with the nitrogen to which they are attached are a heterocyclyl group. R$^9$ for each occurrence is, independently, —H, a substituted or unsubstituted aliphatic group, or a thiol protecting group. R$^{11}$ and R$^{12}$ are each, independently, —H, a substituted or unsubstituted aryl group, a substituted or unsubstituted heteroaryl group, a substituted or unsubstituted aliphatic group, a substituted or unsubstituted aralkyl group, a substituted or unsubstituted heteroaralkyl group or an amine protecting group. Alternatively, R$^{11}$ and R$^{12}$ taken together with the nitrogen to which they are attached form a heterocyclyl group. q is an integer from 1 to about 6. s is 0 or a positive integer. Preferably, s is 0, 1 or 2, and most preferably 0. Each B, independently, is —H, a natural or unnatural nucleobase, protected nucleobase, protected natural or unnatural nucleobase, heterocycle or a protected heterocycle.

Nucleoside bases include naturally occurring bases, such as adenine, guanine, cytosine, thymine, and uracil and modified bases such as 7-deazaguanine, 7-deaza-8-azaguanine, 5-propynylcytosine, 5-propynyluracil, 7-deazaadenine, 7-deaza-8-azaadenine, 7-deaza-6-oxopurine, 6-oxopurine, 3-deazaadenosine, 2-oxo-5-methylpyrimidine, 2-oxo-4-methylthio-5-methylpyrimidine, 2-thiocarbonyl-4-oxo-5-methylpyrimidine, 4-oxo-5-methylpyrimidine, 2-amino-purine, 5-fluorouracil, 2,6-diaminopurine, 8-aminopurine, 4-triazolo-5-methylthymine, 4-triazolo-5-methyluracil and hypoxanthine.

A protected nucleoside base is a nucleoside base in which reactive functional groups of the base are protected. Similarly, a protected heterocycle is a heterocycle in which reactive substitutents of the heterocycle are protected. Typically, nucleoside bases or heterocycles have amine groups which can be protected with an amine protecting group, such as an amide or a carbamate. For example, the amine groups of adenine and cytosine are typically protected with benzoyl protecting groups, and the amine groups of guanine is typically protected with an isobutyryl group, a 4-isopropylphenoxyacetyl group or t-butylphenoxyacetyl group. However, other protection schemes, such as formamidine, may be used. For example, for fast deprotection, the amine groups of adenine and guanine are protected with phenoxyacetyl groups and the amine group of cytosine is protected with an isobutyryl group or an acetyl group. Conditions for removal of the nucleobase or heterocycle protecting group will depend on the protecting group used. When an amide protecting group is used, it can be removed by treating the oligonucleotide with a base solution, such as a concentrated ammonium hydroxide solution, n-methylamine solution or a solution of t-butylamine in ammonium hydroxide.

Amine, hydroxy and thiol protecting groups are known to those skilled in the art. For examples of amine protecting groups see Greene, et al., *Protective Groups in Organic Synthesis* (1991), John Wiley & Sons, Inc., pages 309-405, the teachings of which are incorporated herein by reference in their entirety. Preferably, amines are protected as amides or carbamates. For examples of hydroxy protecting groups see Id., pages 10-142, the teachings of which are incorporated herein by reference in their entirety. Examples of protecting groups which may be employed include silyl groups, especially trialkyl, for example tri(C$_{1-4}$alkyl)silyl groups. A preferred silyl protecting group is a t-butyldimethylsilyl group. A preferred hydroxy protecting group is t-butyldimethylsilyl group. For examples of thiol protecting groups see Id., pages 277-308, the teachings of which are incorporated herein by reference in their entirety.

An acid labile protecting group is a protecting group which can be removed by contacting the group with a Bronsted or a Lewis acid. Acid labile protecting groups are known to those skilled in the art. Examples of common acid labile protecting groups include substituted or unsubstituted trityl groups (Id., pages 60-62), substituted or unsubstituted tetrahydropyranyl groups (Id., pages 31-34), substituted or unsubstituted tetrahydrofuranyl groups (Id., pages 36-37) or pixyl groups (Id., page 65). Trityl groups are commonly substituted by electron donating substituents such as alkoxy groups. A preferred acid labile protecting group is a substituted or unsubstituted trityl, for example 4,4'-dimethoxytrityl (hereinafter "DMT").

A base labile protecting group is a protecting group which can be removed by contacting the group with a Bronsted or a Lewis base. Base labile protecting groups are known to those skilled in the art. Examples of common base labile protecting groups include carbonyl compounds, such as acetyl, benzoyl and pivaloyl groups.

It will be recognised that, whilst the formula 2 is expressed in terms of the natural, nucleosidic configuration (D-isomers) of the given alcohols, the present invention is equally applicable to the corresponding synthetic or unnatural configuration (L-isomers) of the alcohols, and to mixtures of both configurations.

Phosphitylation agents that can be employed in the process of the present invention commonly have the general chemical formula:

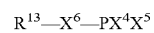

wherein R$^{13}$ represents a phosphorus protecting group, commonly a cleavable phosphorus protecting group employed in oligonucleotide synthesis, for example a substituted or unsubstituted aliphatic or aralkyl group, such as a methyl group, —CH$_2$CH$_2$—Si(CH$_3$)$_2$C$_6$H$_5$, —CH$_2$CH$_2$—S(O)$_2$—CH$_2$CH$_3$, —CH$_2$CH$_2$—C$_6$H$_4$—NO$_2$ and preferably a group of formula —CH$_2$CH$_2$CN; a substituted or unsubstituted aromatic group, such as a phenyl or substituted phenyl, for example a 4-chlorophenyl, 2-chlorophenyl, 2-nitrophenyl or 4-nitrophenyl group; X$^6$ represents O or S, and preferably O; X$^4$ and X$^5$, which may be the same of different, represent leaving groups, such as halo, commonly bromo or chloro, or —NR$^{14}$R$^{15}$, wherein R$^{14}$ and R$^{15}$ each independently represents an alkyl, preferably a C$_{1-6}$ alkyl, group, or R$^{14}$ and R$^{15}$ are joined, together with the N to which they are attached, to form a 5-7 membered ring. Commonly, at least one of X$^4$ and X$^5$ is a group of formula —NR$^{14}$R$^{15}$. Most preferably, X$^4$ and X$^5$ are the same, and it is particularly preferred that both X$^4$ and X$^5$ are —N[CH(CH$_3$)$_2$]$_2$ groups. It is especially preferred that X$^6$ is O and R$^{13}$ —CH$_2$CH$_2$CN.

The process of the present invention is particularly suited to the preparation of phosphoramidites, particularly nucleoside or oligonucleotide phosphoramidites.

Examples of preferred phosphitylating agents include O-β-cyanoethyl-N,N,N',N'-tetraisopropylphosphorodiamidite, (commonly known as "tetraphos"), O-β-cyanoethyl-N,N,N',N'-tetramethylphosphorodiamidite, O-β-cyanoethyl-N,N,N',N'-tetraethylphosphorodiamidite, bis (N,N-diisopropylamino)-2-methyltrifluoroacetylamino-ethoxyphosphine, bis (N,N-diisopropylamino)-2-diphenylmethylsilylethoxyphosphine and O-β-cyanoethyl-bis (N-morpholino) phosphorodiamidite.

The process according to the present invention is often carried out at a temperature in the range of from 0° C. to about 50° C., and preferably at ambient temperature, such as from about 15° C. to about 30° C.

Advantageously, substantially anhydrous reaction conditions are employed.

In many embodiments the process of the present invention is carried out under an inert atmosphere, such as a nitrogen or argon atmosphere.

The process according to the present invention is advantageously employed to produce nucleoside phosphoramidites. Accordingly, a preferred aspect of the present invention comprises a process for the preparation of a compound of formula:

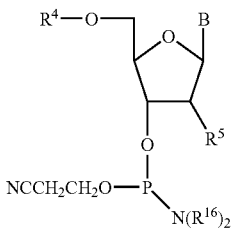

which comprises reacting a compound of formula:

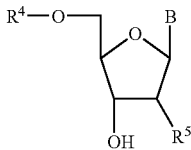

wherein $R^4$ is as previously defined, preferably a dimethoxytrityl group, and $R^5$ is as previously defined;

with a compound of formula:

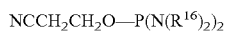

wherein $R^{16}$ represents a $C_{1-6}$ alkyl group, preferably an isopropyl group; in the presence of an activator, where the activator comprises a compound of formula:

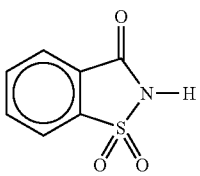

and an organic base.

In many embodiments, the activator is employed at a stoichiometric or sub-stoichiometric mole ratio to the alcohol, with mole ratios of activator to alcohol of from about 0.4:1 to 1:1, particularly from about 0.5:1 to 0.75:1 being preferred.

The phosphitylating agent is often employed at a stoichiometric mole ratio to the alcohol, or in excess, with mole ratios of phosphitylating agent to alcohol of from about 1:1 to 3:1, particularly from about 1:1 to 1.5:1, being preferred.

In the presence of an organic base, the activators employed in the present invention have good solubility particularly in organic solvents that are typically used for phosphitylation. The concentration of the activator and the organic base can be up to the solubility of the activator in the solvent concerned. In a preferred embodiment, the activator and the organic base are present in a concentration range of about 0.01 M to about 2M, for example from about 0.05M to about 0.5M. Commonly, the activator and the organic base are present at a concentration of up to 0.25M, such as from about 0.1M to about 0.25M. In a more preferred embodiment, the activator and the organic base are present in the same molar concentration. In certain embodiments, the organic solvent is a chlorocarbon, such as dichloromethane. In a preferred embodiment, the organic solvent comprises acetonitrile. In another preferred embodiment, the organic solvent comprises an organic amide, such as dimethylformamide, 1-methyl-2-pyrrolidinone or 1,3-dimethyl-2-imidazolidinone.

An organic base is an organic compound that has a tendency to accept protons at pH 7. Preferred organic bases are secondary amines, tertiary amines or azaheterocyclyl compounds, each of which may be substituted or unsubstituted by one or more substituents. An aprotic organic base is an organic base that has no hydrogen bonding protons in its chemical structure before accepting a proton. Aprotic organic bases such as tertiary amines and aprotic azaheterocyclyl compounds are preferably used in conjunction with compounds of formula 1, as described herein, to promote phosphitylation reactions.

Azaheterocyclyl compounds, as used herein, include heteroaryl groups which have one or more nitrogen atom in the aromatic ring and heteroalicyclyl groups that have at least one nitrogen atom in the non-aromatic ring system. Preferably, azaheteroaryl compounds have five- or six-membered aromatic rings with from one to three nitrogens in the aromatic ring. Preferably, azaheteroalicyclyl compounds are five- or six-membered rings, commonly comprising one or two nitrogens in the ring. Preferred azaheterocyclyl compounds are organic bases. Examples of azaheterocyclyl compounds that are organic bases include pyrimidines, 1-alkylpyrazoles, especially 1-($C_{1-4}$ alkyl)pyrazoles, 1-arylpyrazoles, 1-benzylpyrazoles, pyrazines, N-alkylpurines, especially N-($C_{1-4}$ alkyl)purines, N-arylpurines, N-benzylpurines, N-alkylpyrroles, especially N-($C_{1-4}$ alkyl)pyrroles, N-arylpyrroles, N-benzylpyrroles, pyridines, N-alkylimidazoles, especially N-($C_{1-4}$ alkyl)imidazoles, N-arylimidazoles, especially N-phenylimidazole, N-benzylimidazoles, quinolines, isoquinolines, quinoxalines, quinazolines, N-alkylindoles, especially N-($C_{1-4}$ alkyl)indoles, N-arylindoles, N-benzylindoles, N-alkylbenzimidazoles especially N-($C_{1-4}$ alkyl)benzimidazoles, N-arylbenzimidazoles, N-benzylbenzimidazoles, triazine, thiazole, 1-alkyl-7-azaindoles, especially 1-($C_{1-4}$ alkyl)-7-azaindoles, 1-aryl-7-azaindole 1-benzyl-7-azaindoles, pyrrolidines, morpholines, piperidines, and piperazines. Especially preferred azaheterocyclyl compounds are pyridines, such as pyridine and 3-methylpyridine, and N-($C_{1-4}$ alkyl) imidazoles, such as N-methylimidazole.

Tertiary amines are organic bases that have a nitrogen atom which is bonded to three carbon atoms, often to three aryl, commonly phenyl, and/or alkyl groups, commonly to three alkyl groups, including for example trialkylamines such as trimethylamine, triethylamine, and diisopropylethylamine. In addition, tertiary amines can be azaheterocyclyl groups wherein the nitrogen atom is aprotic. Tertiary amines that are azaheterocyclyl groups are preferred. Examples of azaheterocyclyl tertiary amines are N-alkylpyrrolidines, N-arylpyrrolidines, N-alkylpyrroles, N-arylpyrroles, N-alkylmorpholines, N-arylmorpholines, N-alkylpiperidines, N-arylpiperidines, N,N-dialkylpiperazines, N,N-diarylpiperazines, N-alkyl-N-aryl-piperazines, quinuclidines, 1,5-diazabicyclo[4.3.0]non-5-enes and 1,8-diazabicyclo[5.4.0]undec-7-enes. Tertiary amines can also be azaheteroaryl or azaheteroalicyclyl compounds.

Secondary amines are organic bases comprising a nitrogen bonded to a single hydrogen and to two carbon atoms. Commonly the nitrogen atom is bonded to two alkyl or aryl groups or forms part of an azaheterocyclic group. Examples of secondary amine compounds include diethylamine and diisopropylamine.

Particularly preferred organic bases include pyridine, 3-methylpyridine, and N-methylimidazole.

Suitable substituents for aliphatic groups, aryl groups, aralkyl groups, heteroaryl groups, azaheteroaryl groups and heteroalicyclyl groups include aryl groups, halogenated aryl groups, alkyl groups, halogenated alkyl (e.g. trifluoromethyl and trichloromethyl), aliphatic ethers, aromatic ethers, benzyl, substituted benzyl, halogens, particularly chloro and fluoro groups, cyano, nitro, —S-(aliphatic or substituted aliphatic group), and —S-(aromatic or substituted aromatic).

Aliphatic groups, as used herein, include straight chained or branched $C_1$-$C_{1-18}$ hydrocarbons which are completely saturated or which contain one or more unconjugated double bonds, or cyclic $C_3$-$C_{18}$ hydrocarbons which are completely saturated or which contain one or more unconjugated double bonds. Alkyl groups are straight chained or branched $C_1$-$C_8$ hydrocarbons or $C_3$-$C_8$ cyclic hydrocarbons which are completely saturated. Aliphatic groups are preferably alkyl groups.

Aryl groups include carbocyclic aromatic ring systems (e.g., phenyl) and carbocyclic aromatic ring systems fused to one or more carbocyclic aromatic (e.g., naphthyl and anthracenyl) or an aromatic ring system fused to one or more non-aromatic ring (e.g., 1,2,3,4-tetrahydronaphthyl).

Heterocyclic groups, as used herein, include heteroaryl groups and heteroalicyclyl groups. Heteroaryl groups, as used herein, include aromatic ring systems that have one or more heteroatoms selected from sulfur, nitrogen or oxygen in the aromatic ring. Preferably, heteroaryl groups are five or six membered ring systems having from one to four heteroatoms. A heteroalicyclyl group, as used herein, is a non-aromatic ring system that preferably has five to six atoms and includes at least one heteroatom selected from nitrogen, oxygen, and sulfur. Examples of heterocyclic groups include morpholinyl, piperidinyl, piperazinyl, thiomorpholinyl, pyrrolidinyl, thiazolidinyl, tetrahydrothienyl, azetidinyl, tetrahydrofuryl, dioxanyl and dioxepanyl thienyl, pyridyl, thiadiazolyl, oxadiazolyl, indazolyl, furans, pyrroles, imidazoles, pyrazoles, triazoles, pyrimidines, pyrazines, thiazoles, isoxazoles, isothiazoles, tetrazoles, oxadiazoles, benzo(b)thienyl, benzimidazole, indole, tetrahydroindole, azaindole, indazole, quinoline, imidazopyridine, purine, pyrrolo[2,3-d]pyrimidine, and pyrazolo[3,4-d]pyrimidine.

An aralkyl group, as used herein, is an aromatic substituent that is linked to a moiety by an alkyl group. Preferred aralkyl groups include benzyl groups.

A heteroaralkyl group, as used herein, is a heteroaryl substituent that is linked to a moiety by an alkyl group.

The present invention is illustrated without limitation by the following Examples.

EXAMPLE 1

The N-methylimidazole salt of saccharin was prepared by the following procedure. Saccharin was suspended in acetonitrile, and 1.1 eq. of N-methylimidazole with respect to the saccharin was added dropwise to the suspension. The reaction mixture was concentrated under reduced pressure to form the crystalline salt which was washed with either ether or hexane to remove traces of N-methylimidazole and acetonitrile.

EXAMPLE 2

A series of nucleosides was phosphitylated using O-β-cyanoethyl-N,N,N',N'-tetraisopropylphosphoramidite and the N-methylimidazole salt of saccharin as activator.

General Method:

In an appropriate sized flask was added the nucleoside (1.5 mmol) and the solid was dried azeotropically by distilling (rotary evaporator) two times with 20 mL of pyridine. The flask was purged with Ar and to the flask was added 15 mL of acetonitrile. The mixture was stirred at room temperature until a clear solution was obtained. To the mixture was added O-β-cyanoethyl-N,N,N',N'-tetraisopropylphosphoramidite (Tetraphos) followed by the addition of N-methylimidazole salt of saccharin. The mixture was stirred at room temperature while the reaction was monitored for end of reaction by HPLC. At the end of the reaction, the mixture was diluted with 30 mL of ethyl acetate and the organic mixture was washed with 2×25 mL of saturated aqueous sodium bicarbonate and 25 mL of saturated aqueous sodium chloride. The organic layer was separated and dried over $MgSO_4$. The suspension was filtered and the solvent was removed using a rotary evaporator. The residue was dried under vacuum to give a foam.

TABLE 1

Results of amidite synthesis

| Tetraphos (eq.) | Activator (eq.) | nucleoside | Rxn time (h) | % amidite[a] (HPLC) | yield[b] (%) |
|---|---|---|---|---|---|
| 1.2 | 0.6 | 5'-DMT-N-Bz-deoxyA | 7 | 91.9 | 84 |
| 1.2 | 0.5 | 5'-DMT-N-Bz-deoxyA | 5 | 91.5 | 86 |
| 1.2 | 1.0 | 5'-DMT-N-Bz-deoxyA | 5 | 89.8 | 87 |
| 1.2 | 0.5 | 5'-DMT-N-iBu-deoxyG | 16 | 79.1 | 85 |
| 1.2 | 0.5 | 5'-DMT-N-Ac-2'-OMeC | 5 | 89.3 | 85 |
| 1.2 | 0.6 | 5'-DMT-N-Bz-deoxyC | 8 | 91.1 | 79 |
| 1.2 | 0.6 | 5'-DMT-2'-TBDMS-L-U | 16 | 82.6 | 82 |
| 1.2 | 0.6 | 5'-DMT-N-iBu-2'-TBDMS-L-G | 16 | 59.3 | 84 |
| 2.2 | 0.6 | 5'-DMT-N-iBu-2'-TBDMS-L-G | 16 | 87.4 | 82 |

[a]% amidite = % amidite in crude product
[b]yield = yield of crude product

EXAMPLE 2

In a 500 mL round bottom flask was added 5'-DMT-N-Bz-2'-deoxyadenosine (18.00 g, 27.37 mmol) and the solid was dried azeotropically by the addition and evaporation (rotary evaporator) of 2×200 mL of toluene. The residue was dried under vacuum for 16 h. The residue was dissolved in acetonitrile (180 mL) under an argon atmosphere and O-β-cyanoethyl-N,N,N',N'-tetraisopropylphosphorodiamidite (9.90 g, 32.84 mmol) was added. The mixture was stirred for 5 minutes and solid N-methylimidazole salt of saccharin (3.63 g, 13.69 mmol) was added. The mixture was stirred at room temperature while the reaction was monitored by HPLC. After 18 h, no further reaction was observed. To the reaction mixture was added ethyl acetate (200 mL) and the organic solution was washed with saturated aqueous sodium bicarbonate (2×150 mL) and saturated aqueous sodium chloride (150 mL). The organic layer was separated and dried over MgSO$_4$. The suspension was filtered and the solvent was removed using a rotary evaporator. The residue was dried under vacuum for 16 h to give a white foam.

Crude yield: 23.70 g
HPLC: 92.5%

The crude material (23.70 g) was chromatographed using a silica gel (230 g) column. The column was loaded using 30% ethyl acetate/hexanes containing 0.5% triethylamine. The column was washed with 2 column volumes of 30% ethyl acetate/hexanes. The crude material was loaded and the column was eluted using 2 column volumes of 30% ethyl acetate/hexanes, 2 column volumes of 40% ethyl acetate/hexanes, 2 column volumes of 50% ethyl acetate/hexanes and finally 3 column volumes of 70% ethyl acetate/hexanes. Fractions were collected when the product was detected by TLC (8:3 ethyl acetate:hexanes). Fractions containing the desired product were combined and the solvent was removed using a rotary evaporator. The residue was dried under vacuum for 16 h to give a white foam.

Yield: 17.55 g (75%)

HPLC: 97.5%

$^{31}$P NMR: 99.3%

The invention claimed is:

1. A process for the phosphitylation of an alcohol or thiol with a phosphitylation agent in the presence of an activator, characterised in that the activator has the formula 1:

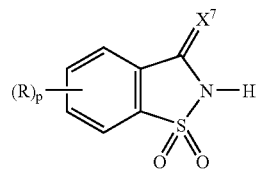

wherein p is 0 or an integer from 1 to 4, R for each occurrence is a substituent, and $X^7$ is O or S.

2. A process according to claim 1, wherein $X^7$ is O and p is 0.

3. A process according to claim 1 or 2, wherein the compound of formula 1 is employed as a salt complex with an organic base.

4. A process according to claim 3, wherein the organic base is selected from the group consisting of pyridine, 3-methylpyridine, and N-methylimidazole.

5. A process according to claim 3, wherein the alcohol or thiol is a nucleoside or oligonucleotide comprising a free hydroxy or thiol group.

6. A process according to claim 5, wherein a nucleoside comprising a free 3'-hydroxy group is phosphitylated.

7. A process according to claim 3, wherein the phosphitylation agent has the general chemical formula:

$$R^{13}-X^6-PX^4X^5$$

wherein $R^{13}$ represents a phosphorus protecting group, $X^6$ represents O or S, $X^4$ and $X^5$, which may be the same of different, represent leaving groups.

8. A process according to claim 7, wherein $R^{13}$ represents a substituted or unsubstituted aliphatic or aralkyl group or a substituted or unsubstituted aromatic group, $X^6$ is O and $X^4$ and $X^5$ each independently represent —NR$^{14}$R$^{15}$, wherein $R^{14}$ and $R^{15}$ each independently represents a $C_{1-6}$ alkyl, group, or $R^{14}$ and $R^{15}$ are joined, together with the N to which they are attached, to form a 5-7 membered ring.

9. A process according to claim 8, wherein the phosphitylating agent is selected from the group consisting of O-β-cyanoethyl-N,N,N',N'-tetraisopropylphosphorodiamidite, O-β-cyanoethyl-N,N,N',N'-tetramethylphosphorodiamidite, O-β-cyanoethyl-N,N,N',N'-tetraethylphosphorodiamidite, bis (N,N-diisopropylamino)-2-methyltrifluoroacetylamino-ethoxyphosphine, bis (N,N- diisopropylamino)-2-diphenylmethylsilylethoxyphosphine and O-β-cyanoethyl-bis (N-morpholino) phosphorodiamidite.

10. A process for the preparation of a compound of formula:

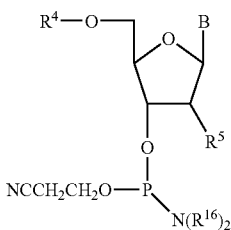

which comprises reacting a compound of formula:

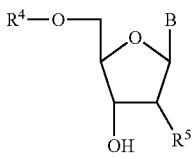

with a compound of formula:

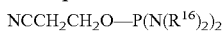

in the presence of an activator, where the activator comprises a compound of formula:

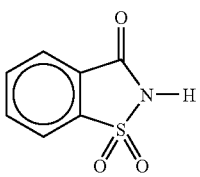

and an organic base, wherein $R^4$ is an alcohol protecting group, $R^5$ is —H, —F —$OR^6$, —$NR^7R^8$, —$SR^9$, or a substituted or unsubstituted aliphatic group, such as methyl or allyl, $R^6$ for each occurrence is —H, a substituted or unsubstituted aliphatic group, a substituted or unsubstituted aryl group, a substituted or unsubstituted aralkyl, an alcohol protecting group, or —$(CH_2)_q$—$NR^{11}R^{12}$, $R^7$ and $R^8$ are each, independently, —H, a substituted or unsubstituted aliphatic group, or an amine protecting group or $R^7$ and $R^8$ taken together with the nitrogen to which they are attached are a heterocyclyl group, $R^9$ is —H, a substituted or unsubstituted aliphatic group, or a thiol protecting group, $R^{11}$ and $R^{12}$ are each, independently, —H, a substituted or unsubstituted aryl group, a substituted or unsubstituted heteroaryl group, a substituted or unsubstituted aliphatic group, a substituted or unsubstituted aralkyl group, a substituted or unsubstituted heteroaralkyl group or an amine protecting group or $R^{11}$ and $R^{12}$ taken together with the nitrogen to which they are attached form a heterocyclyl group, q is an integer from 1 to about 6, B is —H, a natural or unnatural nucleobase, protected nucleobase, protected natural or unnatural nucleobase, heterocycle or a protected heterocycle and $R^{16}$ represents a $C_{1-6}$ alkyl group, preferably an isopropyl group.

11. A process according to claim 10, wherein the organic base is selected from the group consisting of pyridine, 3-methylpyridine, and N-methylimidazole.

12. A process according to claim 10 or 11, wherein $R^5$ is H, OMe or $OCH_2CH_2OMe$.

13. A process according to claim 10 or 11, wherein $R^4$ is an acid-labile protecting group and $R^5$ is $OR^6$ wherein $R^6$ is a base labile protecting group or a silyl protecting group.

* * * * *